(12) United States Patent
Fritz et al.

(10) Patent No.: US 8,900,564 B2
(45) Date of Patent: Dec. 2, 2014

(54) VACCINE COMPOSITION COMPRISING AN ANTIGEN AND A PEPTIDE HAVING ADJUVANT PROPERTIES

(75) Inventors: Jörg Fritz, Vienna (AT); Frank Mattner, Vienna (AT); Wolfgang Zauner, Vienna (AT); Eszter Nagy, Vienna (AT); Michael Buschle, Perchtoldsdorf (AT)

(73) Assignee: Valneva Austria GmbH, Vienna (AT)

( * ) Notice: Subject to any disclaimer, the term of this patent is extended or adjusted under 35 U.S.C. 154(b) by 1148 days.

(21) Appl. No.: 12/124,785

(22) Filed: May 21, 2008

(65) Prior Publication Data

US 2009/0123486 A1 May 14, 2009

Related U.S. Application Data

(63) Continuation of application No. 10/399,442, filed as application No. PCT/EP01/12041 on Oct. 18, 2001.

(30) Foreign Application Priority Data

Oct. 18, 2000 (AT) ........................................ 1789/00

(51) Int. Cl.
| | | |
|---|---|---|
| *A61K 38/00* | (2006.01) | |
| *A61K 38/04* | (2006.01) | |
| *A61K 38/08* | (2006.01) | |
| *A61K 38/27* | (2006.01) | |
| *A61K 39/00* | (2006.01) | |
| *A61K 45/00* | (2006.01) | |
| *A61K 48/00* | (2006.01) | |
| *C07K 7/06* | (2006.01) | |
| *A61K 39/39* | (2006.01) | |
| *C07K 4/00* | (2006.01) | |

(52) U.S. Cl.
CPC ......... *C07K 7/06* (2013.01); *A61K 2039/55516* (2013.01); *A61K 39/0011* (2013.01); *A61K 39/39* (2013.01)
USPC .................... 424/85.1; 424/184.1; 424/278.1; 514/1.1; 514/11.4; 514/21.6; 514/44 R; 514/49

(58) Field of Classification Search
None
See application file for complete search history.

(56) References Cited

U.S. PATENT DOCUMENTS

| | | | |
|---|---|---|---|
| 6,261,568 B1 * | 7/2001 | Gicquel et al. ............. | 424/200.1 |
| 6,312,731 B1 * | 11/2001 | Staas et al. .................... | 424/501 |
| 7,704,514 B2 | 4/2010 | Buschle et al. | |
| 2002/0072495 A1 | 6/2002 | Chertov et al. ................. | 514/12 |
| 2005/0063978 A1 | 3/2005 | Fritz et al. | |
| 2006/0263386 A1 | 11/2006 | Buschle et al. | |
| 2007/0031446 A1 | 2/2007 | Buschle et al. | |
| 2007/0041998 A1 | 2/2007 | Buschle et al. | |

FOREIGN PATENT DOCUMENTS

| | | |
|---|---|---|
| EP | 0905141 | 3/1999 |
| JP | 7070187 | 3/1995 |
| JP | 8134096 | 5/1996 |
| WO | WO 95/04542 | 2/1995 |
| WO | WO 2004/084938 | 10/2004 |

OTHER PUBLICATIONS

Smeltzer and Gillaspy (Poultry Science, 2000, 79: 1042-1049).*
Alvarez-Bravo et al., "Novel synthetic antimicrobial peptides effective against methicillin-resistant *Staphylococcus aureus*," *Biochem J.*, 302:535-538, 1994.
Banchereau and Steinman, "Dendritic cells and the control of immunity," *Nature*, 392:245-252, 1998.
Berger et al., "Circulation and homing of melanoma-reactive T cells to both cutaneous and visceral metastases after vaccination with monocyte-derived dendritic cells," *Int. J. Cancer*, 111:229-237, 2004.
Boman, "Innate immunity and the normal microflora," *Immunol. Rev.*, 173:5-16, 2000.
Brossart and Bevan, "Presentation of exogenous protein antigens on major histocompatability complex class I molecules by dendritic cells: pathway of presentation and regulation by cytokines," *Blood*, 90:1594-1599, 1997.
Buschle et al., "Chemically defined, cell-free cancer vaccines: use of tumor antigen-derived peptides or polyepitope proteins for vaccination," *Gene Ther. Mol. Biol.*, 1:309-321, 1998.
Buschle et al., "Transloading of tumor antigen-derived peptides into antigen-presenting cells," *Proc. Natl. Acad. Sci., USA*, 94:3256-3261, 1997.
Cho et al. "Activation of human neutrophils by a synthetic antimicrobial peptide, KLKLLLLLKLK—$NH_2$, via cell surface calreticulin," *Eur. J. Biochem.*, 266:878-885, 1999.
Cox and Coulter, "Adjuvants—a classification and review of their modes of action," *Vaccines*, 15(3):248-256, 1997.
Encyclopedia Britannica Online, www.search.eb.com/eb/print?eu=76559, 2004.
Fahey et al., "Status of immune-based therapies in HIV infection and AIDS," *Clinical Experimental Immunology*, 88:1-5, 1992.
Ganz and Lehrer, "Antimicrobial peptides from higher eukaryotes: biology and applications," *Mol. Med. Today*, 5:292-297, 1999.

(Continued)

*Primary Examiner* — Gerald R Ewoldt
*Assistant Examiner* — Marianne Dibrino
(74) *Attorney, Agent, or Firm* — Wolf, Greenfield & Sacks, P.C.

(57) ABSTRACT

The invention relates to a vaccine which comprises at least one antigen and a peptide comprising a sequence $R_1$—XZX$Z_N$XZX—$R_2$, whereby N is a whole number between 3 and 7, preferably 5, X is a positively charged natural and/or non-natural amino acid residue, Z is an amino acid residue selected from the group consisting of L, V, I, F and/or W, and $R_1$ and $R_2$ are selected independently one from the other from the group consisting of —H, —$NH_2$, —$COCH_3$, —COH, a peptide with up to 20 amino acid residues or a peptide reactive group or a peptide linker with or without a peptide; X—$R_2$ may also be an amide, ester or thioester of the C-terminal amino acid residue, as well as the use of said peptide for enhancing a patient's adaptive immune response to an antigen.

15 Claims, 3 Drawing Sheets

(56) References Cited

OTHER PUBLICATIONS

Ganz and Lehrer, "Antimicrobial peptides of leukocytes," *Curr. Opinion in Hematology*, 4:53-58, 1997.

Ganz and Lehrer, "Antimicrobial peptides of vertebrates," *Curr. Opinion in Immunology*, 10:41-44, 1998.

Gudmundsson and Agerberth, "Neutrophil antibacterial peptides, multifunctional effector molecules in the mammalian immune system," *J. of Immunol. Methods*, 232:45-54, 1999.

Harding, "Class I MHC presentation of exogenous antigens," *J. Clin Immunol.*, 16:90-97, 1996.

Harding, "Phagocytic processing of antigens for presentation by MHC molecules," *Trends in Cell Biol.*, 5:105-109, 1995.

International Search Report issued in International Application No. PCT/EP01/12041, mailed Apr. 5, 2002.

Letvin, "Progress in the development of an HIV-1 vaccine," *Science*, 280:1875-1880, 1998.

Machuca et al., "Human immunodeficiency virus type 2 infection in Spain. The HIV-2 Spanish Study Group," *Intervirology*, 42:37-42, 1998.

Merck Manual, 16th edition, *Merck Research Laboratories*, Rahway, N.J., p. 21, 1992.

Mizukawa et al., "Presence of defensin in epithelial langerhans cells adjacent to oral carcinomas and precancerous lesions," *Anticancer Res.*, 19:2969-2972, 1999.

Monaco, "A molecular model of MHC class-I-restricted antigen processing," *Immunol. Today*, 13:173-179, 1992.

Nakajima et al., "Chemotherapeutic activity of synthetic antimicrobial peptides: correlation between chemotherapeutic activity and neutrophil-activating activity," *FEBS Letters*, 415:64-66, 1997.

Oxenius et al., "CpG-containing oligonucleotides are efficient adjuvants for induction of protective antiviral immune responses with T-cell peptide vaccines," *J. Virol.*, 73(5):4120-4126, 1999.

Schijns, "Immunological concepts of vaccines adjuvant activity," *Curr. Opinion Immunology*, 12:456-463, 2000.

Schmidt et al., "Cell-free tumor antigen peptide-based cancer vaccines," *Proc. Natl. Acad. Sci., USA*, 94:3262-3267, 1997.

Weiner et al., "Immunostimulatory oligodeoxynucleotides containing the CpG motif are effective as immune adjuvants in tumor antigen immunization," *PNAS*, 94:10833-10837, 1997.

Yang et al., "LL-37, the neutrophil granule- and epithelial cell-derived cathelicidin, utilizes formyl peptide receptor-like 1 (FPRL1) as a receptor to chemoattract human peripheral blood neutrophils, monocytes, and T cells," *J. Exp. Med.*, 192(7):1069-1074, 2000.

Zanetti et al., "The cathelicidin family of antimicrobial peptide precursors: a component of the oxygen-independent defense mechanisms of neutrophils," *Annals New York Academy of Sciences*, 832:147-162, 1997.

Zubay, In: *Biochemistry*, Chapter 1:60-63, 1983.

Office Action issued in U.S. Appl. No. 10/399,442, prepared by Marianne Dibrino, mailed Apr. 4, 2007, pp. 1-19.

Office Action issued in U.S. Appl. No. 10/399,442, prepared by Marianne Dibrino, mailed Nov. 16, 2007, pp. 1-14.

Office Action issued in U.S. Appl. No. 10/399,442, prepared by Marianne Dibrino, mailed Nov. 20, 2006, pp. 1-6.

Office Action issued in U.S. Appl. No. 10/399,442, prepared by Marianne Dibrino, mailed Oct. 5, 2006, pp. 1-5.

Bodey et al., Failure of cancer vaccines: the significant limitations of this approach to immunotherapy. Anticancer Res. Jul.-Aug. 2000;20(4):2665-76.

Gao et al., Tumor vaccination that enhances antitumor T-cell responses does not inhibit the growth of established tumors even in combination with interleukin-12 treatment: the importance of inducing intratumoral T-cell migration. J Immunother. Nov.-Dec. 2000;23(6):643-53.

Marchand et al., Biological and clinical developments in melanoma vaccines. Expert Opin Biol Ther. May 2001;1(3):497-510.

Marchand et al., Tumor regressions observed in patients with metastatic melanoma treated with an antigenic peptide encoded by gene MAGE-3 and presented by HLA-A1. Int J Cancer. Jan. 18, 1999;80(2):219-30.

Xiang et al., An autologous oral DNA vaccine protects against murine melanoma. Proc Natl Acad Sci U S A. May 9, 2000;97(10):5492-7.

\* cited by examiner

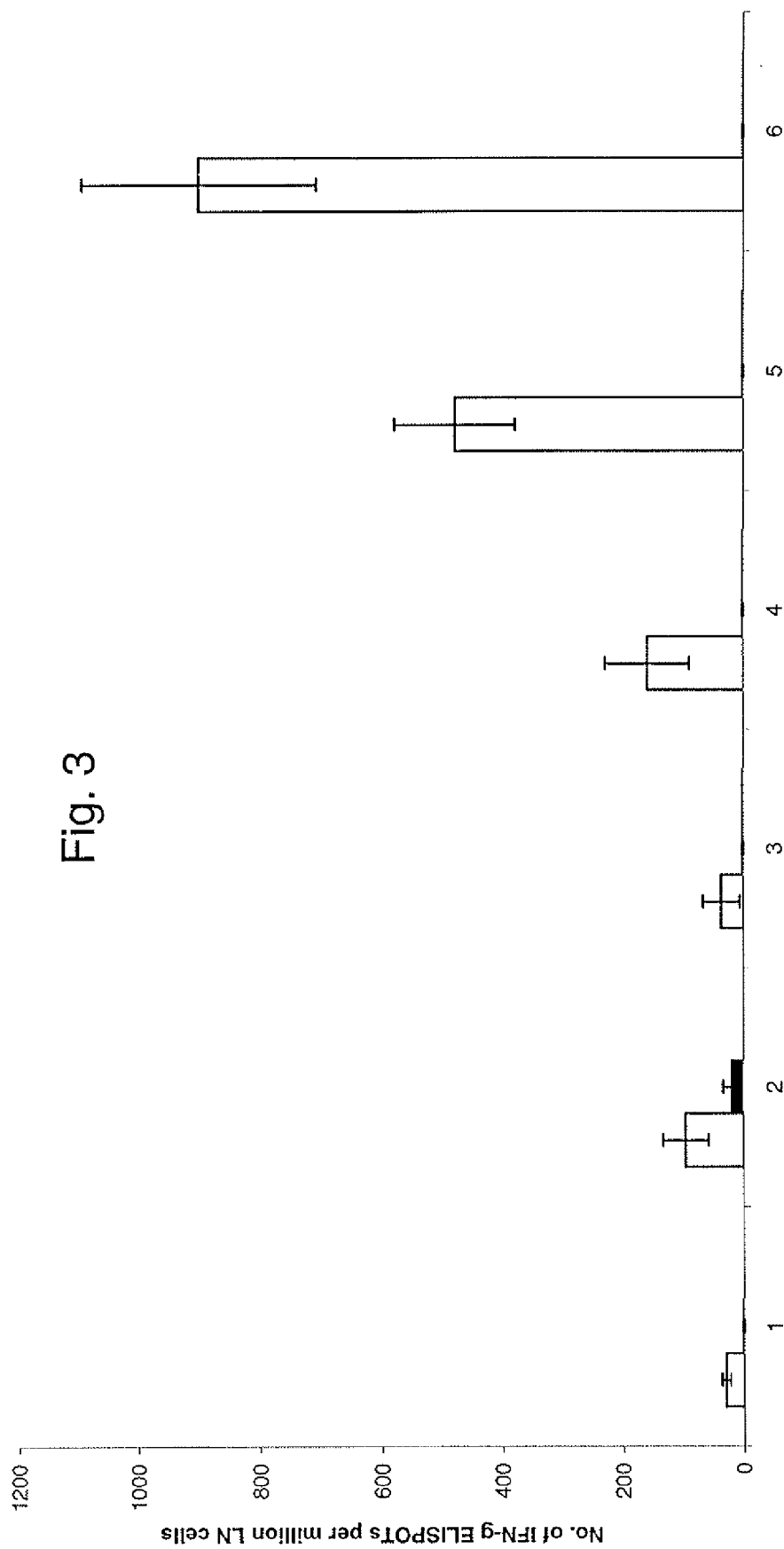

VACCINE COMPOSITION COMPRISING AN ANTIGEN AND A PEPTIDE HAVING ADJUVANT PROPERTIES

CROSS-REFERENCE TO RELATED APPLICATIONS

This application is a continuation of U.S. application Ser. No. 10/399,442, filed on Apr. 17, 2003, which is a U.S. national phase application under 35 U.S.C. §371 of PCT Application No. PCT/EP01/12041 filed 18 Oct. 2001, which claims priority to Austrian Application No. A 1789/00 filed 18 Oct. 2000. The entire contents of these applications is incorporated herein by reference.

BACKGROUND

The present invention relates to vaccines comprising at least one antigen and an immunostimulating substance.

Host protection from invading pathogens involves cellular and humoral effectors and results from the concerted action of both non-adaptive (innate) and adaptive (acquired) immunity. The latter is based on specific immunological recognition mediated by receptors, is a recent acquisition of the immune system, and is present only in vertebrates. The former evolved before the development of adaptive immunity, consisting of a variety of cells and molecules distributed throughout the organism with the task of keeping potential pathogens under control (Boman, H. (2000)), (Zanetti, M. (1997)).

B and T lymphocytes are the mediators of acquired antigen-specific adaptive immunity, including the development of immunological memory, which is the main gbal of creating a successful vaccine (Schijns, V. (2000)). Antigen presenting cells (APCs) are highly specialized cells that can process antigens and display their processed fragments on the cell surface together with molecules required for lymphocyte activation. This means that APCs are very important for the initiation of specific immune reactions. The main APCs for T lymphocyte activation are dendritic cells (DCs), macrophages, and B cells, whereas the main APCs for B cells are follicular dendritic cells. In general DCs are the most powerful APCs in terms of initiation of immune responses stimulating quiescent naive and memory B and T lymphocytes.

The natural task of APCs in the periphery (e.g. DCs or Langerhans cells) is to capture and process antigens, thereby being activated they start to express lymphocyte co-stimulatory molecules, migrate to lymphoid organs, secrete cytokines and present antigens to different populations of lymphocytes, initiating antigen-specific immune responses. They not only activate lymphocytes, under certain circumstances, they also tolerize T cells to antigens (Banchereau, J. (1998)).

Antigen recognition by T lymphocytes is major histocompatibility complex (MHC)-restricted. A given T lymphocyte will recognize an antigen only when the peptide is bound to a particular MHC molecule. In general, T lymphocytes are stimulated only in the presence of self MHC molecules, and antigen is recognized only as peptides bound to self MHC molecules. MHC restriction defines T lymphocyte specificity in terms of the antigen recognized and in terms of the MHC molecule that binds its peptide fragment.

Intracellular and extracellular antigens present quite different challenges to the immune system, both in terms of recognition and of appropriate response. Presentation of antigens to T cells is mediated by two distinct classes of molecules—MHC class I (MHC-I) and MHC class II (MHC-II), which utilize distinct antigen processing pathways. Mainly one could distinguish between two major antigen processing pathways that have evolved. Peptides derived from intracellular antigens are presented to $CD8^+$ T cells by MHC class I molecules, which are expressed on virtually all cells, while extracellular antigen-derived peptides are presented to $CD4^+$ T cells by MHC-II molecules (Monaco, J. (1992); Harding, C. (1995)). However, there are certain exceptions to this dichotomy. Several studies have shown that peptides generated from endocytosed particulate or soluble proteins are presented on MHC-I molecules in macrophages as well as in dendritic cells (Harding, C. (1996); Brossart, P. (1997)). Therefore APCs like dendritic cells sitting in the periphery, exerting high potency to capture and process extracellular antigens and presenting them on MHC-I molecules to T lymphocytes are interesting targets in pulsing them extracellularily with antigens in vitro and in vivo.

The important and unique role of APCs, including stimulating activity on different types of leukocytes, is reflecting their central position as targets for appropriate strategies in developing successful vaccines. Theoretically one way to do so is to enhance or stimulate their natural task, the uptake of antigen(s). Once pulsed with the appropriate antigens the vaccine is directed against, APCs should start to process the taken up antigen(s), thereby being activated, expressing lymphocyte co-stimulatory molecules, migrating to lymphoid organs, secreting cytokines and presenting antigens to different populations of lymphocytes thereby initiating immune responses.

Activated T cells generally secrete a number of effector cytokines in a highly regulated fashion, e.g. interleukin 2 (IL-2), IL-4, IL-5, IL-10 and interferon-$\gamma$ (IFN-$\gamma$). The functional detection of cytotoxic T lymphocyte responses to specific antigens (e.g. tumor antigens, in general antigens administered in a vaccine) is commonly monitored by an ELISpot assay (enzyme-linked immunospot assay), a technique analyzing cytokine production at the single cell level. In the present invention an ELISpot assay for the cellular immunity promoting cytokine IFN-$\gamma$ was used to monitor successful peptide-specific T cell activation.

It has previously been shown that polycations efficiently enhance the uptake of MHC class I-matched peptides into tumor cells, a peptide or protein pulsing process which was called "TRANSloading" (Buschle, M. (1997)). Furthermore, we have shown that polycations are able to "TRANSload" peptides or proteins into antigen presenting cells in vivo as well as in vitro (Buschle, M. (1998)). In addition, co-injection of a mixture of poly-L-arginine or poly-L-lysine together with an appropriate peptide as a vaccine protects animals from tumor growth in mouse models (Schmidt, W. (1997)). This chemically defined vaccine is able to induce a high number of antigen/peptide-specific T cells. That was shown to be at least partly attributable to an enhanced uptake of peptides into APCs mediated by the polycation (Buschle, M. (1998)) indicating that APCs when pulsed in vivo with antigens can induce T cell-mediated immunity to the administered antigen.

As opposed to adaptive immunity, which is characterized by a highly specific but relatively slow response, innate immunity is based on effector mechanisms that are triggered by differences in the structure of microbial components relative to the host. These mechanisms can mount a fairly rapid initial response, which mainly leads to neutralization of the noxious agents. Reactions of innate immunity are the only defense strategy of lower phyla and have been retained in vertebrates as a first line host defense before the adaptive immune system is mobilized.

In higher vertebrates the effector cells of innate immunity are neutrophils, macrophages, and natural killer cells and probably also dendritic cells (Mizukawa, N. (1999)), whereas the humoral components in this pathway are the complement cascade and a variety of different binding proteins (Boman, H. (2000)).

A rapid and effective component of innate immunity is the production of a large variety of microbicidal peptides with a length of usually between about 12 and about one hundred amino acid residues. Several hundred different antimicrobial peptides have been isolated from a variety of organisms, ranging from sponges, insects to animals and humans, which points to a widespread distribution of these molecules. Antimicrobial peptides are also produced by bacteria as antagonistic substances against competing organisms.

In EP 0 905 141 A1 a peptide fragment of a limulus anti-LPS factor (LALF) having antiviral action is disclosed. This LALF peptide does not specifically enhance an immune response but enhances the non-specific defenses of mononuclear cells and can also be used in a prophylactic way or further the peptide can also be administered topically to a wound site to stimulate an enhanced wound healing and repair.

Main sources of antimicrobial peptides are granules of neutrophils and epithelial cells lining the respiratory, gastrointestinal and genitourinary tracts. In general they are found at those anatomical sites most exposed to microbial invasion, are secreted into internal body fluids or stored in cytoplasmic granules of professional phagocytes (neutrophils) (Ganz, T. (1997); Ganz, T. (1998); Ganz, T. (1999); Boman, H. (2000); Gudmundsson, GH. (1999)).

It has been shown previously (Austrian patent application A 1416/2000) that naturally occurring, cathelicidin-derived antimicrobial peptides or derivatives thereof have an immune response stimulating activity and therefore constitute highly effective adjuvants.

BRIEF SUMMARY OF THE INVENTION

The aim of the present invention is to provide an adjuvant/ "carrier peptide" that is able to strongly enhance the immune response to a specific co-administered antigen and therefore constitutes a highly effective adjuvant.

This object is solved by a vaccine which comprises at least one antigen and a peptide comprising a sequence $R_1$—XZXZX$Z_N$XZXR$_2$, (SEQ ID NOS:23-27, wherein xzxzzzxzx=SEQ ID NO:23; xzxzzzzxzx=SEQ ID NO:24; xzxzzzzzxzx=SEQ ID NO:25; xzxzzzzzzxzx=SEQ ID NO:26; and xzxzzzzzzzxzx=SEQ ID NO:27), (hereinafter termed as "peptide A"), whereby N is a whole number between 3 and 7, preferably 5, X is a positively charged natural and/or non-natural amino acid residue, Z is an amino acid residue selected from the group consisting of L, V, I, F and/or W, and $R_1$ and $R_2$ are selected independently one from the other from the group consisting of —H, —NH$_2$, —COCH$_3$, —COH, a peptide with up to 20 amino acid residues or a peptide reactive group or a peptide linker with or without a peptide; X—$R_2$ may also be an amide, ester or thioester of the C-terminal amino acid residue.

Besides naturally occurring antimicrobial peptides, synthetic antimicrobial peptides have been produced and investigated. The synthetic antimicrobial peptide KLKLLLLLKLK-NH$_2$ (SEQ ID NO: 1) was shown to have significant chemotherapeutic activity in Staphylococcus aureus-infected mice; human neutrophils were activated to produce the superoxide anion ($O_2^-$) via cell surface calreticulin.

The exact number and position of K and L was found to be critical for the antimicrobial activity of the synthetic peptide (Nakajima, Y. (1997); Cho, J-H. (1999)).

It has now been surprisingly shown within the course of the present invention that peptides according to the present invention comprising a sequence $R_1$—XZXZ$_N$XZX—$R_2$ (SEQ ID NOS:23-27, wherein xzxzzzxzx=SEQ ID NO:23; xzxzzzzxzx=SEQ ID NO:24; xzxzzzzzxzx=SEQ ID NO:25; xzxzzzzzzxzx=SEQ ID NO:26; and xzxzzzzzzzxzx=SEQ ID NO:27), whereby N is a whole number between 3 and 7, preferably 5, X is a positively charged natural and/or non-natural amino acid residue, Z is an amino acid residue selected from the group consisting of L, V, I, F and/or W, and $R_1$ and $R_2$ are selected independently one from the other from the group consisting of —H, —NH$_2$, —COCH$_3$, —COH, a peptide with uP to 20 amino acid residues or a peptide reactive group or a peptide linker with or without a peptide; X—$R_2$ may also be an amide or ester (or even thioester) of the C-terminal amino acid residue TRANSload antigenic peptides or proteins into APCs far more efficiently than known adjuvants, including naturally occurring antimicrobial peptides. They further have a strong immune response stimulating activity and therefore constitute highly effective adjuvants.

Preferably, the C-terminus is not modified (COOH or COO$^-$), since this form is even better than the amidated form of the peptide.

In the scope of the present invention the sequence may be amidated at its carboxy-end or carry a further amino acid sequence, however, preferably the carboxy-end is free.

Furthermore, in the scope of the present invention, all the X comprised in the peptides alpha may represent the same amino acid residue. Preferably, however, in one peptide alpha X represents only one specific amino acid residue, e.g. either K or R, etc. The same can be applied with respect to Z: all the Z in the peptides alpha may be one single amino acid species or different amino acid species: e.g. either L or V etc. This is especially the case for the $Z_N$-portion in the middle of the formula, which may be e.g. $L_5$ (SEQ ID NO: 36) or $L_3$ as well as LVIFW (SEQ ID NO: 19), LILFLLIW (SEQ ID NO: 20), WIF, $W_3L_2$ (SEQ ID NO:21), and all other combinations in this motive, being between 3 and 7 amino acids at length, preferably from 4 to 6 amino acid residues, especially 5 amino acid residues. These residues are also preferred for the $R_1$ and $R_2$ portion (e.g. that more than 50%, preferably more than 80%, especially more than 90% of $R_1$ and/or $R_2$ are L, I, F, V and/or W, if $R_1$ and/or R, are peptides). Preferably $R_1$ and $R_2$ are the same, advantageously they are both H (i.e. free amino- or carboxy-termini).

Under the scope of the present invention the term "non-natural" comprises any amino acid residue which does not naturally occur and do not occur in natural proteins, respectively.

Peptide $R_1$-KLKL$_5$KLK—$R_2$ (SEQ ID NO:1) is specifically preferred, however also $R_1$-KIKL$_5$KIK—$R_2$ (SEQ ID NO:29), $R_1$-KVKL$_5$KVK—$R_2$ (SEQ ID NO:30), $R_1$-KFKL$_5$KVK—$R_2$ (SEQ ID NO:31), $R_1$-KLKL$_6$KLK—$R_2$ (SEQ ID NO:32), $R_1$-KWKW$_5$KLK—$R_2$ (SEQ ID NO:33), $R_1$-KWKWL$_3$WKWK—$R_2$ (SEQ ID NO:34), $R_1$-KLKL$_4$KLK—$R_2$ (SEQ ID NO:35) or permutations with respect to positions of I, F, V, W and L are advantageous.

Of course, the vaccine may comprise two or more antigens depending on the desired immune response. The antigen(s) may also be modified so as to further enhance the immune response.

Preferably, proteins or peptides derived from viral or bacterial pathogens, from fungi or parasites, as well as tumor antigens (cancer vaccines) or antigens with a putative role in autoimmune disease are used as antigens (including derivatized antigens like glycosylated, lipidated, glycolipidated or hydroxylated anti-gens). Furthermore, carbohydrates, lipids or glycolipids may be used as antigens themselves. The derivatization process may include the purification of a specific protein or peptide from the pathogen, the inactivation of the pathogen as well as the proteolytic or chemical derivatization or stabilization of such a protein or peptide. Alternatively, also the pathogen itself may be used as an antigen. The antigens are preferably peptides or proteins, carbohydrates, lipids, glycolipids or mixtures thereof.

According to a preferred embodiment, T cell epitopes are used as antigens. Alternatively, a combination of T cell epitopes and B cell epitopes may also be preferred.

The antigens to be used in the present compositions are not critical. Also mixtures of different antigens are of course possible to be used according to the present invention. Preferably, proteins or peptides derived from a viral or a bacterial pathogen or from fungi or parasites are used as such antigens (including derivatized antigens or glycosylated or lipidated anti-gens or polysaccharides or lipids). Another preferred source of antigens are tumor antigens. Preferred pathogens are selected from human immunodeficiency virus (HIV), hepatitis A and B viruses, hepatitis C virus (HCV), rous sarcoma virus (RSV), Epstein Barr virus (EBV) Influenza virus, Rotavirus, *Staphylococcus aureus, Chlamydia pneumonias, Chlamydia trachomatis, Mycobacterium tuberculosis, Streptococcus pneumonias, Bacillus anthracis, Vibrio cholerae, Plasmodium* sp. (*Pl. falciparum, Pl. vivax*, etc.), *Aspergillus* sp. or *Candida albicans*. Antigens may also be molecules expressed by cancer cells (tumor antigens). The derivation process may include the purification of a specific protein from the pathogen/cancer cells, the inactivation of the pathogen as well as the proteolytic or chemical derivatization or stabilisation of such a protein. In the same way also tumor antigens (cancer vaccines) or autoimmune antigens may be used in the pharmaceutical composition according to the present invention. With such compositions a tumor vaccination or a treatment for autoimmune diseases may be performed.

In the case of peptide antigens the use of peptide mimotopes/agonists/superagonists/antagonists or peptides changed in certain positions without affecting the immunologic properties or non-peptide mimotopes/agonists/superagonists/antagonists is included in the current invention. Peptide antigens may also contain elongations either at the carboxy or at the amino terminus of the peptide antigen facilitating interaction with the polycationic compound(s) or the immunostimulatory compound(s). For the treatment of autoimmune diseases peptide antagonists may be applied.

Antigens may also be derivatized to include molecules enhancing antigen presentation and targeting of antigens to antigen presenting cells.

In one embodiment of the invention the pharmaceutical composition serves to confer tolerance to proteins or protein fragments and peptides which are involved in autoimmune diseases. Antigens used in this embodiments serve to tolerize the immune system or downregulate immune responses against epitopes involved in autoimmune processes.

Preferably, the antigen is a peptide consisting of 5 to 60, preferably 6 to 30, especially 8 to 11, amino acid residues. Antigens of this length have been proven to be especially suitable for T cell activation. The antigens can further be coupled with a tail, e.g. according to A 657/2000, U.S. Pat. No. 5,726,292 or WO98/01558.

The antigen may be mixed with the peptides of the present invention or otherwise specifically formulated e.g. as liposome, retard formulation, etc. The antigen may also be covalently or non-covalently bound to the peptide according to the present invention. Preferably, the antigens are covalently bound to the peptide as $R_1$ or $R_2$ residues or to side chains of the amino acid residues of the peptide, especially to the K and R side chain.

The relative amounts of the ingredients of the present composition are highly dependent on the necessities of the individual composition. Preferably between 10 ng and 1 g of antigen and peptide alpha are applied. Preferred amounts of antigen/peptide alpha lie in the range of 0.1 to 1000 μg antigen per vaccination and 0.1 to 1000 μg peptide A. The composition according to the present invention may further contain auxiliary substances, such as buffers, salts, stabilizers, immunostimulants, antioxidants, etc., or other effective substances, such as antiinflammators or antinociceptive drugs.

The present compositions may be applied to a patient, e.g. a vaccination candidate, in efficient amounts, e.g. at weekly, biweekly or monthly intervals. Patients to be treated with the present composition may also be vaccinated repeatedly or only once. A preferred use of the present invention is the active immunization, especially of humans or animals without protection against the specific antigen.

The present composition may be applied subcutaneously, intramuscularly, rectally, intravenally, intradermally, intrapinnally, transdermally as well as by oral uptake.

Of course, the vaccine according to the present invention can comprise any further substance, as for example any other pharmaceutically acceptable carrier, etc. The vaccine according to the present invention may be formulated according to known methods, e.g. as i.v. vaccines, DNA vaccines, transdermal vaccines, topical vaccines, intranasal vaccines and as combination vaccines. The dosages may be selected by standard processes for vaccines which are improvements of known vaccines, however, a lower dosage than the known vaccine is possible for the same protection and therefore preferred.

Preferably, the vaccine is provided in a storage-stable form, e.g. lyophilized, optionally provided in combination with a suitable reconstitution solution.

The amino acid residues according to the present invention may be D- or L-amino acids. Preferably, all or at least more than 80% of the residues belong to only one species (D or L). Most preferred, all amino acids in the peptide according to the present invention are of the same species (D or L). In some forms, the peptide according to the present invention may also comprise additional amino acid residues inserted in the sequence of peptide alpha, however, no A, G and T residues should be contained in the hydrophobic portion ($Z$, $Z_N$) of the peptide.

Preferably, in the peptide sequence X is an amino acid residue selected from the group consisting of K, R, ornithine and/or homoarginine. Again the X of one peptide alpha can be different amino acid residues selected from this group however, it is preferable that X is either K or R or ornithine or homoarginine in one peptide alpha.

According to a preferred embodiment of the present invention in the peptide sequence X is K. The peptide alpha comprising this amino acid as X has been shown to be particularly strong in inducing an immune response.

Preferably, in the peptide sequence Z is selected from the group consisting of L, V, I, F and/or W. As mentioned for X, also the Z can represent in one peptide alpha different amino acid residues. However, it is preferred that Z of one peptide alpha is only one amino acid residue, e.g. either L or V or I or F or W, whereby L and I residues are most preferred followed by F, followed by V and followed by W (L>I>F>V>W).

Still preferred, in the peptide alpha sequence Z is L (or I, especially L). Thereby, the peptide alpha is able to induce a particularly strong immune response.

Most preferred the peptide alpha is H-KLKLLLLLKLK-H (SEQ ID NO: 1). Of course, also the physiological form of this peptide (e.g. with a protonated N-terminus ($NH_3^+$) and a deprotonated C-terminus ($COO^-$)) shall be deemed to be incorporated in this formula (as for all peptides according to the present invention).

According to a further advantageous embodiment, in the peptide sequence $R_1$ and/or $R_2$ is/are 10 to 20 amino acid residues. Thereby a peptide alpha is provided which has a length with which a particularly strong immune response is induced or improved.

According to an advantageous embodiment of the present invention, the amino acid residues of $R_1$ and/or $R_2$ are non-negatively charged amino acid residues.

Again, the amino acid residues can be natural and/or non-natural amino acid residues. By adding non-negatively charged amino acid residues at either one or both ends of the peptide alpha this peptide shows a strong capability for improving or inducing an immune response.

Preferably, $R_1$ and/or $R_2$ form a hydrophobic tail for the peptide A. Therefore, the amino acid residues of $R_1$ and/or $R_2$ are preferably selected from the group consisting of L, V, I, F and/or W. Still preferred, the amino acid residues of $R_1$ and/or $R_2$ are selected from the group consisting of L, I and/or F. Most preferred the additional amino acid residues are L. These peptides alpha show a particularly strong capability of inducing a higher immune response.

According to a preferred embodiment of the present invention the amino acid residues of $R_1$ and/or $R_2$ are positively charged natural and/or non natural amino acid residues. Preferably, the additional amino acid residues are selected from the group consisting of K, R, ornithine and/or homoarginine. Still preferred the amino acid residues of $R_1$ and/or $R_2$ are K. These peptides alpha also show a particularly good capability of improving the immune response.

It is preferred, that the amino acid residues of $R_1$ and/or $R_2$ are selected from the first group (consisting of L, V, I, F and/or W) or the second group (consisting of positively charged amino acid residues). However, it is also possible, that the amino acid residues of $R_1$ and/or $R_2$ are selected from both groups for one single peptide alpha.

The peptide may be linked to the peptide alpha core of the present invention by normal peptide bounds or via peptide reactive groups or peptide linkers. Peptide reactive groups are chemical groups suitable for binding peptides or proteins. Therefore, the N- or C-terminus of the present peptide alpha may be chemically modified to comprise a chemical modification (e.g. iminothioane, 3-mercaptopropionyl, . . . ) allowing the covalent attachment of a peptide or an antigen, respectively. Alternatively, peptide alpha may comprise a suitable peptide linker, i.e. a linker molecule being able to form a link between the core peptide alpha (e.g. the peptide without $R_1$ and/or $R_2$) and e.g. an antigen linked or linkable thereto. The peptide according to the present invention may be present with or without the peptide/antigen being bound to the peptide reactive group and/or the peptide linker. Such chemical modifications and suitable peptide linkers are well available to the skilled man in the art.

Preferably, the vaccine comprises at least one further immune response stimulating substance. As immune response stimulating substance any substance or molecule can be used which is known to be active as an adjuvant. Such substances are disclosed in WO93/19768. Other substances may be e.g. polycations, as for example polylysine or polyarginine. Other adjuvants may be components in the form of particles, e.g. silicagel or dextran beads, which are sufficiently small so that they can enter into the cells. The addition of this further immune response stimulating substance will render the vaccine even more efficient.

Preferably the pharmaceutical composition according to the present invention, especially in the form of a vaccine, further comprises a polycationic polymer, preferably a polycationic peptide, especially polyarginine, polylysine or an antimicrobial peptide.

The polycationic compound(s) to be used according to the present invention may be any polycationic compound which shows the characteristic effect according to the WO 97/30721. Preferred polycationic compounds are selected from basic polypeptides, organic polycations, basic polyaminoacids or mixtures thereof. These polyaminoacids should have a chain length of at least 4 amino acid residues. Especially preferred are substances containing peptidic bounds, like polylysine, polyarginine and polypeptides containing more than 20%, especially more than 50% of basic amino acids in a range of more than 8, especially more than 20, amino acid residues or mixtures thereof. Other preferred polycations and their pharmaceutical compositons are described in WO 97/30721 (e.g. polyethyleneimine) and WO 99/38528. Preferably these polypeptides contain between 20 and 500 amino acid residues, especially between 30 and 200 residues.

These polycationic compounds may be produced chemically or recombinantly or may be derived from natural sources.

Cationic (poly)peptides may also be polycationic anti-bacterial microbial peptides. These (poly)peptides may be of prokaryotic or eukaryotic origin or may be produced chemically or recombinantly. Peptides may also belong to the class naturally occurring antimicrobial peptides. Such host defense peptides or defensives are also a preferred form of the polycationic polymer according to the present invention. Generally, a compound allowing as an end product activation (or down-regulation) of the adaptive immune system, preferably mediated by APCs (including dendritic cells) is used as polycationic polymer.

Especially preferred for use as polycationic substance in the present invention are cathelicidin derived antimicrobial peptides or derivatives thereof (A 1416/2000, incorporated herein by reference), especially antimicrobial peptides derived from mammalian cathelicidins, preferably from human, bovine or mouse.

Furthermore, also neuroactive compounds, such as (human) growth hormone (as described e.g. in WO01/24822) may be used as immunostimulants.

Polycationic compounds derived from natural sources include HIVREV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelicidin, especially mouse, bovine or especially human cathelicidins and/or cathelicidins. Related or derived cathelicidin substances contain the whole or parts of the cathelicidin sequence with at least 15-20 amino acid residues. Derivations may include the substitution or modification of the natural amino acids by amino acids which are not among the 20 standard amino acids. Moreover, further cationic residues may be introduced into such cathelicidin molecules. These cathelicidin molecules are preferred to be combined with the antigen/vaccine composition according to the present invention. However, these cathelin molecules surprisingly have turned out to be also effective as an adjuvant for a antigen without the addition of further adjuvants. It is therefore possible to use such cathelicidin molecules as efficient adjuvants in vaccine formulations with or without further immunactivating substances.

Preferably, the immune response stimulating substance is a cytokine. Cytokines play an important role in activating and stimulating B cells, T cells and NK cells, macrophages, dendritic cells and various other cells participating in inducing immune responses. Any cytokine can be used which will additionally enhance the immune response to the antigen(s).

Preferably, the vaccine according to the present invention further comprises an immunostimulating/immunogenic nucleic acid, preferably an oligodeoxynucleotide containing deoxyinosine, an oligodeoxynucleotide containing deoxyuridine, an oligodeoxynucleotide containing a methylated or unmethylated CG motif or an inosine and cytidine containing nucleic acid molecule.

The immunogenic nucleic acids to be used according to the present invention can be of synthetic, prokaryotic and eukaryotic origin. In the case of eukaryotic origin, DNA should be derived from, based on the phylogenetic tree, less developed species (e.g. insects, but also others). In a preferred embodiment of the invention the immunogenic oligodeoxynucleotide (ODN) is a synthetically produced DNA-molecule or mixtures of such molecules. Derivates or modifications of ODNs such as thiophosphate substituted analogues (thiophosphate residues substitute for phosphate) as for example described in U.S. Pat. No. 5,723,335 and U.S. Pat. No. 5,663,153, and other derivatives and modifications, which preferably stabilize the immunostimulatory composition(s) but do not change their immunological properties, are also included. A preferred sequence motif is a six base DNA motif containing an (unmethylated) CpG dinucleotide flanked by two 5' purines and two 3' pyrimidines (5'-Pur-Pur-C-G-Pyr-Pyr-3'). The CpG motifs contained in the ODNs according to the present invention are more common in microbial than higher vertebrate DNA and display differences in the pattern of methylation. Surprisingly, sequences stimulating mouse APCs are not very efficient for human cells. Preferred palindromic or non-palindromic ODNs to be used according to the present invention are disclosed e.g. in Austrian Patent applications A 1973/2000, A 805/2001, EP 0 468 520 A2, WO 96/02555, WO 98/16247, WO 98/18810, WO 98/37919, WO 98/40100, WO 98/52581, WO 98/52962, WO 99/51259 and WO 99/56755 all incorporated herein by reference. Apart from stimulating the immune system certain ODNs are neutralizing some immune responses. These sequences are also included in the current invention, for example for applications for the treatment of autoimmune diseases. ODNs/DNAs may be produced chemically or recombinantly or may be derived from natural sources. Preferred natural sources are insects.

Alternatively, also nucleic acids based on inosine and cytidine (as e.g. described in the PCT/EP01/06437) or deoxynucleic acids containing deoxyinosine and/or deoxyuridine residues (described in the Austrian patent applications A 1973/2000 and A 805/2001, incorporated herein by reference) may preferably be used as immunostimulatory nucleic acids for the present invention.

Of course, also mixtures of different immunogenic nucleic acids may be used according to the present invention.

Another aspect of the present invention is the use of the peptide comprising a peptide A sequence as defined above for the preparation of an adjuvant for enhancing the immune response to at least one antigen.

According to a preferred embodiment of the invention, the adjuvant is added to a vaccine. It is of course possible to administer the adjuvant directly to the mammal, e.g. preferably before the vaccination. It is, however, easier for the administration to add the adjuvant to a vaccine which is then administered to the mammal all at once.

According to a further aspect, the present invention relates to a method of vaccinating a mammal including humans against a specific antigen or a group of specific antigens, said method comprising the administration of an effective amount of a vaccine according to the present invention to said mammal, including humans, to be vaccinated. Alternatively, the method comprises administering an effective amount of an adjuvant comprising the peptide alpha as described above, after which a vaccine is administered.

BRIEF DESCRIPTION OF THE DRAWINGS

The invention will be described in more detail by the following examples and figures, but the invention is of course not limited thereto.

In FIG. 2, LALF is SEQ ID NO: 18, KAKAAAAAKAK-NH$_2$ (SEQ ID. No:8); KGKGGGGGKGK-NH$_2$ (SEQ ID. No:9); KTKTTTTTKTK-NH$_2$ (SEQ ID. No:10); KLKLVIF-WKLK-NH$_2$ (SEQ ID. No:11); KVKVVVVVKVK-NH$_2$ (SEQ ID. No:12); KWKWWWWWKWK-NH$_2$ (SEQ ID. No:13); KFKFFFFFKFK-NH$_2$ (SEQ ID. No:14); RLKLLLLLKLR-NH$_2$ (SEQ ID. No:15); RLRLLLLLRLR-NH$_2$ (SEQ ID. No: 16); KLKLLLLLKLK-NH$_2$ (SEQ ID. No:17); KLKLLLLLKLK-COOH (SEQ ID. No. 1).

FIG. 3 shows the amount of IFN-γ-producing cells in mice vaccinated with an antigenic peptide in combination with the (synthetic antimicrobial) peptide KLKLLLLLKLK (SEQ ID NO: 1).

DETAILED DESCRIPTION

Examples

Example 1

TRANSloading Murine Macrophages with a Synthetic Antimicrobial Peptide as "Carrier Peptide"

To test if the (synthetic antimicrobial) peptide KLKLLLLLKLK (SEQ ID NO: 1) is able to function as "carrier-peptide" for antigens, to TRANSload APCs in vitro, which means enhancing the antigen uptake into APCs, a fluorescently labelled peptide was used as antigenic peptide. It was mixed with diverse concentrations of KLKLLLLLKLK (SEQ ID NO: 1) and other previously described "carrier-peptides" as indicated.

To compare the efficiency of peptide delivery of these diverse "carrier-peptides", the amount of peptide uptake into APCs was monitored by incubating P388D1 cells (murine monocyte-macrophage antigen presenting cell line; purchased from ATCC (TIB-63)) for 1 h at 37° C. with a constant amount of fluorescein-tagged peptide alone or in combination with diverse "carrier-peptides" at concentrations indicated.

Before analysing the cells by flow cytometry, the cells were washed extensively to remove free peptide. The relative amount of fluorescein-tagged peptide taken up by the cells was measured by flow cytometry.

The antigenic peptide used is an influenza-haemagglutinin-derived MHC class I (Kd) binding peptide (Buschle, M. (1997)). 2 μg of this fluorescein-tagged antigenic peptide (LFEAIEGFI) (SEQ ID NO:22) were mixed with 3 different amounts of each carrier peptide tested at concentrations representing 101.7, 50.9 and 5.09 nmol positive charges.

Figure 1:
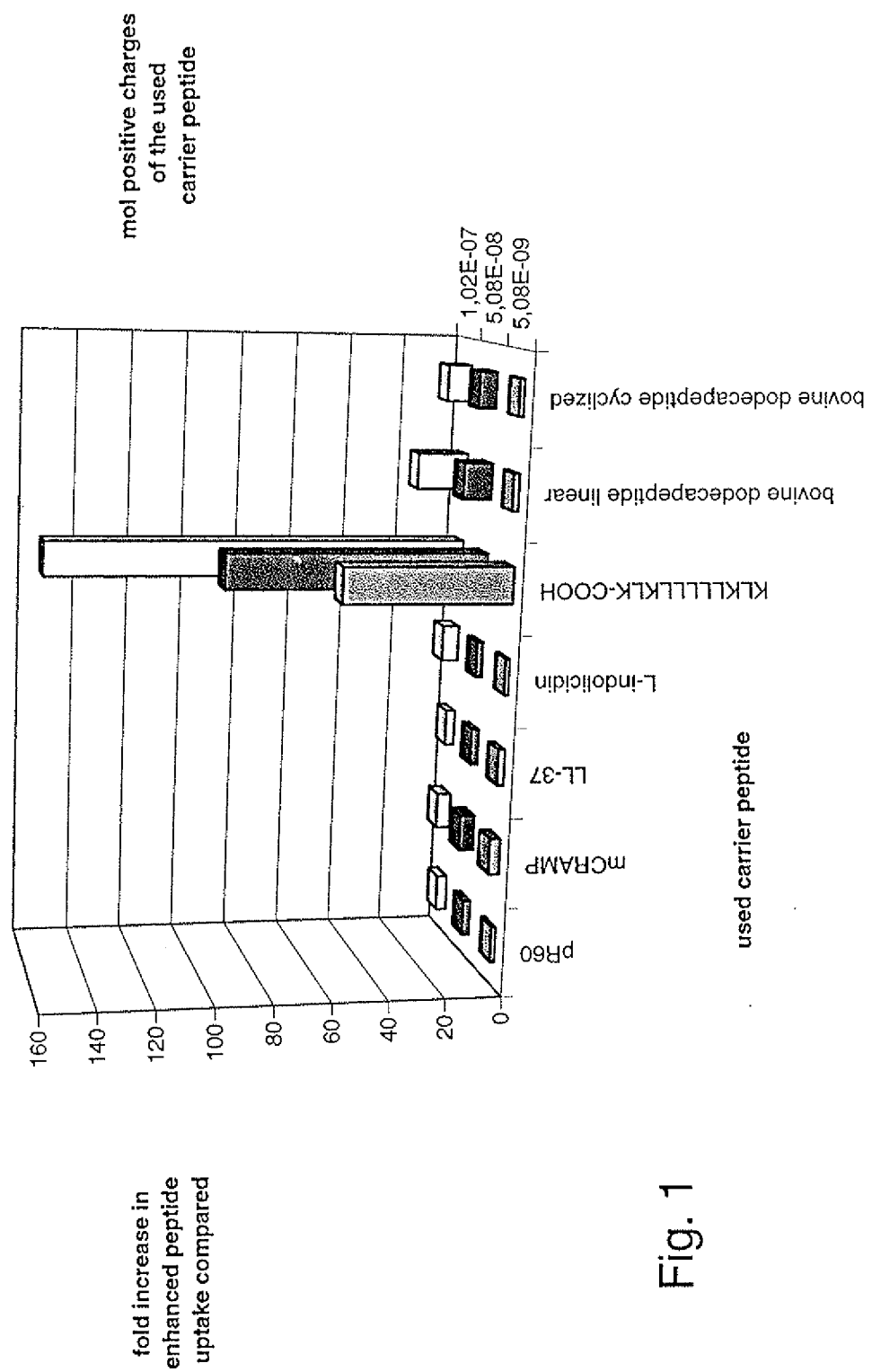
FIG. 1 shows the TRANSloading capacity of the (synthetic antimicrobial) peptide KLKLLLLLKLK (SEQ ID. No. 1) in comparison to diverse, previously described "carrier-peptides".

(FIG. 1 shows the fold increase in enhanced peptide uptake compared to peptide alone):

fluorescein-tagged peptide LFEAIEGFI (SEQ ID NO:22) mixed with (1)+poly-L-arginine (pR 60; 60 mer)
(2)+murine cathelicidin-derived antimicrobial peptide (mCRAMP); SEQ ID. No. 2
(3)+LL-37; SEQ ID. No. 3
(4)+L-indolicidin; SEQ ID. No 4
(5)+KLKLLLLLKLK (free C-terminus); SEQ ID. No. 1
(6)+linear bovine dodecapeptide; SEQ ID. No. 5
(7)+cyclized bovine dodecapeptide Whereas fluorescence is known to be sparse in cells treated with peptide alone (as shown previously), intense fluorescence of "TRANSloaded" cells was especially found in cells which were TRANSloaded with the (synthetic antimicrobial) peptide KLKLLLLLKLK (SEQ ID NO: 1) as "carrier peptide", indicating that it is able to pulse APCs with an antigenic peptide very efficiently.

Example 2

TRANSloading Murine Macrophages with Diverse Synthetic Antimicrobial Peptides as "Carrier Peptides"

Diverse synthetic antimicrobial peptides comprising peptide A sequences were tested to function as "carrier-peptide" for antigens, to TRANSload APCs in vitro, which means enhancing the antigen uptake into APCs. For that purpose, a fluorescent labeled peptide was used as antigenic peptide. It was mixed with diverse concentrations of peptides comprising peptide A sequences and other previously described "carrier-peptides" as indicated.

To compare the efficiency of peptide delivery of these diverse "carrier-peptides", the amount of peptide uptake into APCs was monitored by incubating P388D1 cells (murine monocyte-macrophage antigen presenting cell line; purchased from ATCC (TIB-63) for 1 h at 37° C. with a constant amount of fluorescein-tagged peptide alone or in combination with diverse "carrier-peptides" at concentrations indicated. Before analysing the cells by flow cytometry, the cells were washed extensively to remove free peptide. The relative amount of fluorescein-tagged peptide taken up by the cells was measured by flow cytometry.

Figure 2:
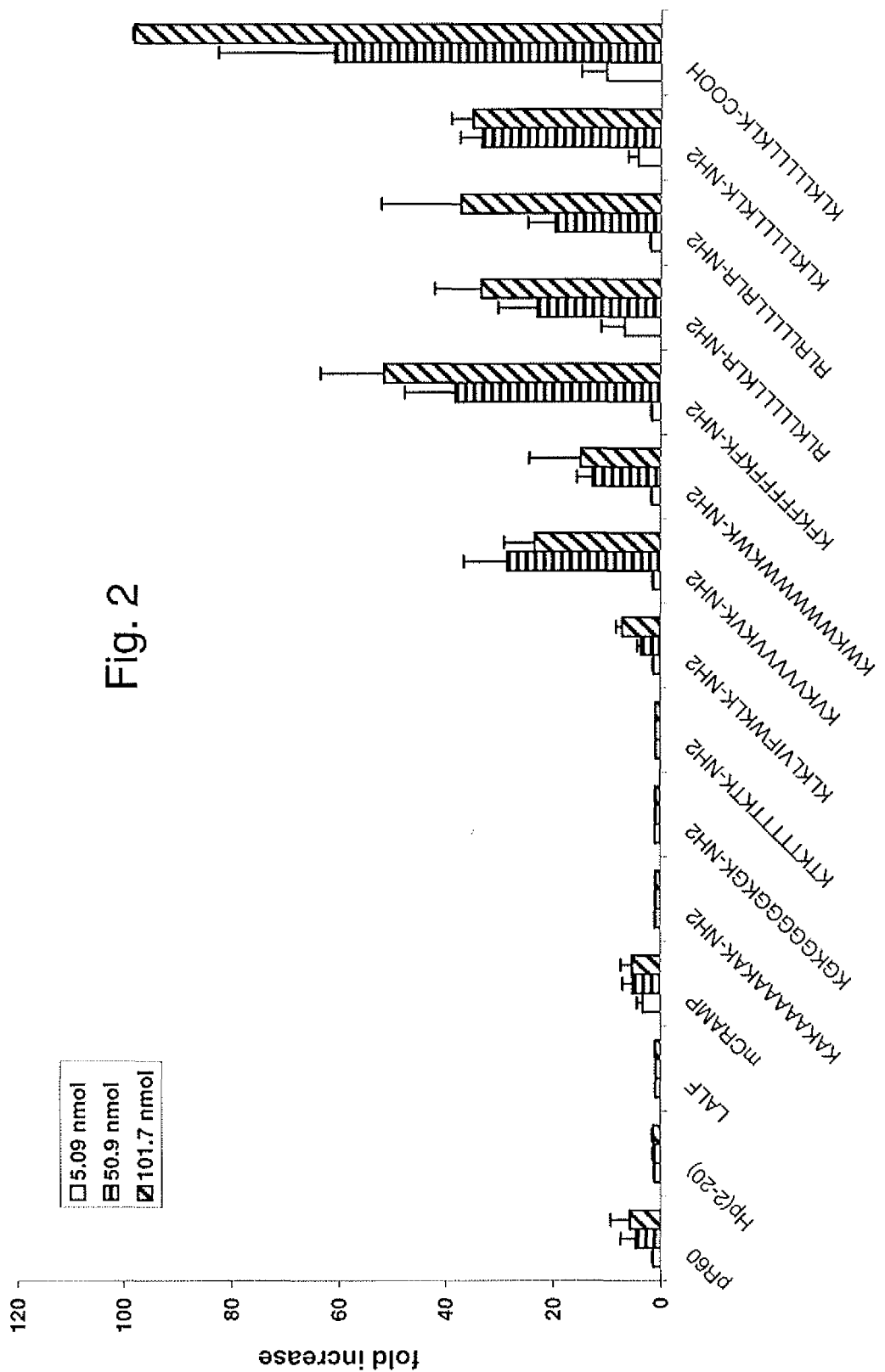
FIG. 2 shows the effectivity of peptide variants according to the present invention compared to other peptides.

The antigenic peptide used is an influenza-haemagglutinin-derived MHC class I (Kd) binding peptide (Buschle, M. (1997)). 3 μg of this fluorescein-tagged antigenic peptide (LFEAIEGFI) (SEQ ID NO:22) were mixed with 3 different amounts of each carrier peptide tested at concentrations representing 101.7, 50.9, and 5.09 nmol positive charges. (FIG. 2 shows the fold increase in enhanced peptide uptake compared to peptide alone):

fluorescein-tagged peptide LFEAIEGFI (SEQ ID NO:22) mixed with (1) poly-L-arginine (60 mer)
(2) Hp(2-20), a cecropin-like antibacterial peptide derived from the ribosomal protein L1 of *Helicobacter pylori*; SEQ ID. No:6
(3) LALF-peptide: SEQ ID No:7
(4) murine cathelicidine-derived antimicrobial peptide; SEQ ID No:2
(5) KAKAAAAAKAK-NH$_2$; SEQ ID. No:8
(6) KGKGGGGGKGK-NH$_2$; SEQ ID. No:9
(7) KTKTTTTTKTK-NH$_2$; SEQ ID. No:10
(8) KLKLVIFWKLK-NH$_2$; SEQ ID. No:11
(9) KVKVVVVVKVK-NH$_2$; SEQ ID. No:12
(10) KWKWWWWWKWK-NH$_2$; SEQ ID. No:13
(11) KFKFFFFFKFK-NH$_2$; SEQ ID. No:14
(12) RLKLLLLLKLR-NH$_2$; SEQ ID. No:15
(13) RLRLLLLLTRLR-NH$_2$; SEQ ID. No: 16
(14) KLKLLLLLKLK-NH$_2$; SEQ ID. No:17
(15) KLKLLLLLKLK-COOH (free C-terminus); SEQ ID. No. 1

Whereas fluorescence is known to be sparse in cells treated with peptide alone (as shown previously), intense fluorescence of "TRANSloaded" cells was especially found in cells which were TRANSloaded with the peptide comprising a peptide A sequence (including the above mentioned preferred embodiments) as "carrier peptide", indicating that the peptides according to the present invention are able to pulse APCs with an antigenic peptide very efficiently.

Example 3

Testing the Ability to Enhance the Induction of Peptide-Specific T Cell Responses in Vivo For testing the ability of the (synthetic antimicrobial) peptide KLKLLLLLKLK (SEQ ID NO: 1) to enhance the induction of peptide-specific T cell responses in vivo, groups of 4 mice (C57BL/6, female, 8 weeks of age, H-2b) were injected subcutaneously into the flank 3 times (days 0, 28, and 56), with an antigenic melanoma peptide (100 μg) derived from TRP-2 (mouse tyrosinase related protein-2) alone or in combination with either poly-L-arginine or the (synthetic antimicrobial) peptide KLKLLL.LKLK (SEQ ID NO: 1) as "carrier peptide". The amounts of the (synthetic antimicrobial) peptide KLKLLLLLKLK (SEQ ID NO: 1) used represent four different amounts at concentrations representing the equal amount (100 μg) of poly-L-arginine in terms of μg, the equal (168 μg), the double (336 μg) and the triple (504 μg) amount of poly-L-arginine in terms of positive charges. The groups of mice were injected as follows (amounts indicated/per mouse).

(1) 100 μg peptide
(2) 100 μg peptide+100 μg poly-L-arginine (pR 60)
(3) 100 μg peptide+100 μg KLKLLLLLKLK (SEQ ID NO: 1)
(4) 100 μg peptide+168 μg KLKLLLLLKLK (SEQ ID NO: 1)
(5) 100 μg peptide+336 μg KLKLLLLLKLK (SEQ ID NO: 1)
(6) 100 μg peptide+504 μg KLKLLLLLKLK (SEQ ID NO: 1)

12 days after the 3$^{rd}$ vaccination, draining (inguinal) lymph nodes were removed and lymph node cells (FIG. 3) were activated ex vivo with TRP-2-derived (mouse tyrosinase related protein-2) peptide to determine IFN-γ-producing specific cells in an ELISpot assay (number of IFN-γ-ELISpots per million lymph node cells).

FIG. 3 shows that injection of mice with peptide plus increasing amounts of KLKLLLLLKLK (SEQ ID NO: 1) resulted in many more IFN-γ-producing specific cells than injection of mice with peptide alone or in combination with poly-L-arginine. It has also been confirmed that the peptide KLKLLLLLKLK (SEQ ID NO: 1) does not elicit IFN-γ-producing peptide-specific T cells (as confirmed by ELISpot-assay), i.e. that only non KLKLLLLLKLK (SEQ ID NO: 1) specific T-cells have been obtained in the present experiments.

This example clearly demonstrates that the (synthetic antimicrobial) peptide KLKLLLLLKLK (SEQ ID NO: 1) enhances the induction of peptide-specific T cell responses in vivo.

In summary, the (synthetic antimicrobial) peptide KLKLLLLLKLK (SEQ ID NO: 1) showed a high "TRANS-loading" and immunostimulating efficiency, indicating that peptides alpha are able to pulse APCs with antigenic peptides in vitro and in vivo very efficiently and are good adjuvants/ "carrier-peptides" for antigenic peptides in inducing adaptive immune responses.

REFERENCES

Banchereau, et al. (1998), "Dendritic cells and the control of immunity", Nature 392(6673): 245-52.

Boman (2000), "Innate immunity and the normal microflora", Immunol. Rev. 173: 5-16.

Brossart, et al. (1997), "Presentation of exogenous protein antigens on major histocompatibility complex class I molecules by dendritic cells: pathway of presentation and regulation by cytokines", Blood 90(4): 1594-9.

Buschle, et al. (1998), "Chemically defined, cell-free cancer vaccines: use of tumor antigen-derived peptides or polyepitope proteins for vaccination", Gene Therapy and molecular Biology 1: 309-21.

Buschle, et al. (1997), "Transloading of tumor antigen-derived peptides into antigen-presenting cells", Proc. Natl. Acad. Sci., USA 94(7): 3256-61.

Cho, et al. (1999), "Activation of human neutrophils by a synthetic anti-microbial peptide, KLKLLLLLKLK-NH, via cell surface calreticulin", Eur. J. Biochem. 266: 878-85.

Ganz, et al. (1997), "Antimicrobial peptides of leukocytes", Curr. Opin. Hematol. 4(1): 53-8.

Ganz, T., (1998), "Antimicrobial peptides of vertebrates", Curr. Opin. Immunol. 10(1): 41-4.

Ganz, et al. (1999), "Antibiotic peptides from higher eukaryotes: biology and applications." Mol. Med. Today 5(7): 292-7.

Gudmundsson, et al. (1999), "Neutrophil antibacterial peptides, multifunctional effector molecules in the mammalian immune system", J. Immunol. Methods 232(1-2): 45-54.

Harding (1995), "Phagocytic processing of antigens for presentation by MHC molecules", Trends in Cell Biology 5(3): 105-09.

Harding (1996), "Class I MHC presentation of exogenous antigens", J. Clin. Immunol. 16(2): 90-6.

Mizukawa, et al. (1999), "Presence of defensin in epithelial Langerhans cells adjacent to oral carcinomas and precancerous lesions", Anticancer Res. 19(4B): 2669-71.

Monaco (1992), "A molecular model of MHC class-I-restricted antigen processing", Immunol. Today 13(5): 173-9.

Nakajima, et al. (1997), "Chemotherapeutic activity of synthetic antimicrobial peptides: correlation between chemotherapeutic activity and neutrophil-activating activity", FEBS Lett. 415: 64-66.

Schijns (2000), "Immunological concepts of vaccine adjuvant activity", Curr. Opin. Immunol. 12(4): 456-63.

Schmidt, et al. (1997), "Cell-free tumor antigen peptide-based cancer vaccines", Proc. Natl. Acad. Sci., USA 94(7): 3262-7.

Zanetti, et al. (1997), "The cathelicidin family of antimicrobial peptide precursors: a component of the oxygen-independent defense mechanisms of neutrophils", Ann. N.Y. Acad. Sc. 832: 147-62.

The invention claimed is:

1. A method of enhancing a patient's adaptive immune response to an antigen comprising:
obtaining at least one antigen;
obtaining at least one peptide comprising a sequence H-KLKLLLLLKLK-H (SEQ ID NO:1; and
administering the antigen and the peptide to a patient.

2. The method of claim 1, wherein the antigen and the peptide are administered to the patient in a single pharmaceutical composition.

3. The method of claim 1, wherein the patient is a human.

4. The method of claim 1, wherein the antigen and the peptide are administered to the patient once.

5. The method of claim 1, wherein the antigen and the peptide are administered to the patient repeatedly.

6. The method of claim 1, wherein the antigen and the peptide are administered subcutaneously.

7. The method of claim 1, wherein the antigen and the peptide are administered intra-muscularly.

8. The method of claim 1, wherein between 0.1 to 1,000 μg of the antigen are administered.

9. The method of claim 1, wherein between 0.1 to 1,000 μg of the peptide are administered.

10. The method of claim 1, wherein enhancing the patient's adaptive immune response to the antigen comprises enhancing uptake of the antigen into an antigen presenting cell.

11. The method of claim 2, further comprising adding at least one further immune response stimulating substance to the single pharmaceutical composition.

12. The method of claim 2, further comprising adding at least one immunostimulatory nucleic acid to the single pharmaceutical composition.

13. The method of claim 12, wherein the immunostimulatory nucleic acid is an oligodeoxynucleotide containing deoxyinosine, an oligodeoxynucleotide containing deoxyuridine, an oligodeoxynucleotide containing at least one CG motif, or an inosine and cytidine containing nucleic acid molecule.

14. The method of claim 2, further comprising adding at least one cytokine to the single pharmaceutical composition.

15. The method of claim 2, further comprising adding at least one polycationic peptide or human growth hormone to the single pharmaceutical composition.

* * * * *

SEQUENCE LISTING

```
<160> NUMBER OF SEQ ID NOS: 36

<210> SEQ ID NO 1
<211> LENGTH: 11
<212> TYPE: PRT
<213> ORGANISM: Artificial
<220> FEATURE:
<223> OTHER INFORMATION: Synthetic Peptide

<400> SEQUENCE: 1

Lys Leu Lys Leu Leu Leu Leu Leu Lys Leu Lys
1               5                   10

<210> SEQ ID NO 2
<211> LENGTH: 31
<212> TYPE: PRT
<213> ORGANISM: Artificial
<220> FEATURE:
<223> OTHER INFORMATION: Synthetic Peptide

<400> SEQUENCE: 2

Arg Leu Ala Gly Leu Leu Arg Lys Gly Gly Glu Lys Ile Gly Glu Lys
1               5                   10                  15
```

Leu Lys Lys Ile Gly Gln Lys Ile Lys Asn Phe Phe Gln Lys Leu
                20                  25                  30

<210> SEQ ID NO 3
<211> LENGTH: 37
<212> TYPE: PRT
<213> ORGANISM: Artificial
<220> FEATURE:
<223> OTHER INFORMATION: Synthetic Peptide

<400> SEQUENCE: 3

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
        35

<210> SEQ ID NO 4
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (13)..(13)
<223> OTHER INFORMATION: AMIDATION

<400> SEQUENCE: 4

Ile Leu Pro Trp Lys Trp Pro Trp Trp Pro Trp Arg Arg
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic Peptide

<400> SEQUENCE: 5

Arg Leu Cys Arg Ile Val Val Ile Arg Val Cys Arg
1               5                   10

<210> SEQ ID NO 6
<211> LENGTH: 19
<212> TYPE: PRT
<213> ORGANISM: Artificial
<220> FEATURE:
<223> OTHER INFORMATION: Synthetic Peptide

<400> SEQUENCE: 6

Ala Lys Lys Val Phe Lys Arg Leu Glu Lys Leu Phe Ser Lys Ile Gln
1               5                   10                  15

Asn Asp Lys

<210> SEQ ID NO 7
<211> LENGTH: 10
<212> TYPE: PRT
<213> ORGANISM: Artificial
<220> FEATURE:
<223> OTHER INFORMATION: Synthetic Peptide

<400> SEQUENCE: 7

Arg Ile Lys Pro Thr Phe Arg Arg Leu Lys

```
                1               5                  10

<210> SEQ ID NO 8
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 8

Lys Ala Lys Ala Ala Ala Ala Ala Lys Ala Lys
1               5                  10

<210> SEQ ID NO 9
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 9

Lys Gly Lys Gly Gly Gly Gly Gly Lys Gly Lys
1               5                  10

<210> SEQ ID NO 10
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 10

Lys Thr Lys Thr Thr Thr Thr Thr Lys Thr Lys
1               5                  10

<210> SEQ ID NO 11
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 11

Lys Leu Lys Leu Val Ile Phe Trp Lys Leu Lys
1               5                  10

<210> SEQ ID NO 12
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
```

```
<222> LOCATION: (11)..(11)
<223> OTHER INFORMATION: AMIDATION

<400> SEQUENCE: 12

Lys Val Lys Val Val Val Val Val Lys Val Lys
1               5                   10

<210> SEQ ID NO 13
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 13

Lys Trp Lys Trp Trp Trp Trp Trp Lys Trp Lys
1               5                   10

<210> SEQ ID NO 14
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 14

Lys Phe Lys Phe Phe Phe Phe Phe Lys Phe Lys
1               5                   10

<210> SEQ ID NO 15
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 15

Arg Leu Lys Leu Leu Leu Leu Leu Lys Leu Arg
1               5                   10

<210> SEQ ID NO 16
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 16

Arg Leu Arg Leu Leu Leu Leu Leu Arg Leu Arg
1               5                   10

<210> SEQ ID NO 17
<211> LENGTH: 11
```

```
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 17

Lys Leu Lys Leu Leu Leu Leu Leu Lys Leu Lys
1               5                   10

<210> SEQ ID NO 18
<211> LENGTH: 4
<212> TYPE: PRT
<213> ORGANISM: Artificial
<220> FEATURE:
<223> OTHER INFORMATION: Synthetic Peptide

<400> SEQUENCE: 18

Leu Ala Leu Phe
1

<210> SEQ ID NO 19
<211> LENGTH: 5
<212> TYPE: PRT
<213> ORGANISM: Artificial
<220> FEATURE:
<223> OTHER INFORMATION: Synthetic Peptide

<400> SEQUENCE: 19

Leu Val Ile Phe Trp
1               5

<210> SEQ ID NO 20
<211> LENGTH: 8
<212> TYPE: PRT
<213> ORGANISM: Artificial
<220> FEATURE:
<223> OTHER INFORMATION: Synthetic Peptide

<400> SEQUENCE: 20

Leu Ile Leu Phe Leu Leu Ile Trp
1               5

<210> SEQ ID NO 21
<211> LENGTH: 5
<212> TYPE: PRT
<213> ORGANISM: Artificial
<220> FEATURE:
<223> OTHER INFORMATION: Synthetic Peptide

<400> SEQUENCE: 21

Trp Trp Trp Leu Leu
1               5

<210> SEQ ID NO 22
<211> LENGTH: 9
<212> TYPE: PRT
<213> ORGANISM: Artificial
<220> FEATURE:
<223> OTHER INFORMATION: Synthetic Peptide

<400> SEQUENCE: 22

Leu Phe Glu Ala Ile Glu Gly Phe Ile
1               5
```

```
<210> SEQ ID NO 23
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: X = any positively charged amino acid
<220> FEATURE:
<221> NAME/KEY: MOD_RES
<222> LOCATION: (2)..(2)
<223> OTHER INFORMATION: X = L, V, I, F or W
<220> FEATURE:
<221> NAME/KEY: MOD_RES
<222> LOCATION: (3)..(3)
<223> OTHER INFORMATION: X = any positively charged amino acid
<220> FEATURE:
<221> NAME/KEY: MOD_RES
<222> LOCATION: (4)..(6)
<223> OTHER INFORMATION: X = L, V, I, F and/or W
<220> FEATURE:
<221> NAME/KEY: MOD_RES
<222> LOCATION: (7)..(7)
<223> OTHER INFORMATION: X = any positively charged amino acid
<220> FEATURE:
<221> NAME/KEY: MOD_RES
<222> LOCATION: (8)..(8)
<223> OTHER INFORMATION: X = L, V, I, F or W
<220> FEATURE:
<221> NAME/KEY: MOD_RES
<222> LOCATION: (9)..(9)
<223> OTHER INFORMATION: X = any positively charged amino acid

<400> SEQUENCE: 23

Xaa Xaa Xaa Xaa Xaa Xaa Xaa Xaa Xaa
1               5

<210> SEQ ID NO 24
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X = any positively charged amino acid
<220> FEATURE:
<221> NAME/KEY: MOD_RES
<222> LOCATION: (2)..(2)
<223> OTHER INFORMATION: X = L, V, I, F or W
<220> FEATURE:
<221> NAME/KEY: MOD_RES
<222> LOCATION: (3)..(3)
<223> OTHER INFORMATION: X = any positively charged amino acid
<220> FEATURE:
<221> NAME/KEY: MOD_RES
<222> LOCATION: (4)..(7)
<223> OTHER INFORMATION: X = L, V, I, F and/or W
<220> FEATURE:
<221> NAME/KEY: MOD_RES
<222> LOCATION: (8)..(8)
<223> OTHER INFORMATION: X = any positively charged amino acid
<220> FEATURE:
<221> NAME/KEY: MOD_RES
<222> LOCATION: (9)..(9)
<223> OTHER INFORMATION: X = L, V, I, F or W
<220> FEATURE:
<221> NAME/KEY: MOD_RES
<222> LOCATION: (10)..(10)
<223> OTHER INFORMATION: X = any positively charged amino acid

<400> SEQUENCE: 24
```

Xaa Xaa Xaa Xaa Xaa Xaa Xaa Xaa Xaa Xaa
1               5                   10

<210> SEQ ID NO 25
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X = any positively charged amino acid
<220> FEATURE:
<221> NAME/KEY: MOD_RES
<222> LOCATION: (2)..(2)
<223> OTHER INFORMATION: X = L, V, I, F or W
<220> FEATURE:
<221> NAME/KEY: MOD_RES
<222> LOCATION: (3)..(3)
<223> OTHER INFORMATION: X = any positively charged amino acid
<220> FEATURE:
<221> NAME/KEY: MOD_RES
<222> LOCATION: (4)..(8)
<223> OTHER INFORMATION: X = L, V, I, F and/or W
<220> FEATURE:
<221> NAME/KEY: MOD_RES
<222> LOCATION: (9)..(9)
<223> OTHER INFORMATION: X = any positively charged amino acid
<220> FEATURE:
<221> NAME/KEY: MOD_RES
<222> LOCATION: (10)..(10)
<223> OTHER INFORMATION: X = L, V, I, F or W
<220> FEATURE:
<221> NAME/KEY: MOD_RES
<222> LOCATION: (11)..(11)
<223> OTHER INFORMATION: X = any positively charged amino acid

<400> SEQUENCE: 25

Xaa Xaa Xaa Xaa Xaa Xaa Xaa Xaa Xaa Xaa Xaa
1               5                   10

<210> SEQ ID NO 26
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X = any positively charged amino acid
<220> FEATURE:
<221> NAME/KEY: MOD_RES
<222> LOCATION: (2)..(2)
<223> OTHER INFORMATION: X = L, V, I, F or W
<220> FEATURE:
<221> NAME/KEY: MOD_RES
<222> LOCATION: (3)..(3)
<223> OTHER INFORMATION: X = any positively charged amino acid
<220> FEATURE:
<221> NAME/KEY: MOD_RES
<222> LOCATION: (4)..(9)
<223> OTHER INFORMATION: X = L, V, I, F and/or W
<220> FEATURE:
<221> NAME/KEY: MOD_RES
<222> LOCATION: (10)..(10)
<223> OTHER INFORMATION: X = any positively charged amino acid
<220> FEATURE:
<221> NAME/KEY: MOD_RES
<222> LOCATION: (11)..(11)
<223> OTHER INFORMATION: X = L, V, I, F or W
<220> FEATURE:
<221> NAME/KEY: MOD_RES
<222> LOCATION: (12)..(12)
<223> OTHER INFORMATION: X = any positively charged amino acid

```
<400> SEQUENCE: 26

Xaa Xaa Xaa Xaa Xaa Xaa Xaa Xaa Xaa Xaa Xaa Xaa
1               5                   10

<210> SEQ ID NO 27
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: X = any positively charged amino acid
<220> FEATURE:
<221> NAME/KEY: MOD_RES
<222> LOCATION: (2)..(2)
<223> OTHER INFORMATION: X = L, V, I, F or W
<220> FEATURE:
<221> NAME/KEY: MOD_RES
<222> LOCATION: (3)..(3)
<223> OTHER INFORMATION: X = any positively charged amino acid
<220> FEATURE:
<221> NAME/KEY: MOD_RES
<222> LOCATION: (4)..(10)
<223> OTHER INFORMATION: X = L, V, I, F and/or W
<220> FEATURE:
<221> NAME/KEY: MOD_RES
<222> LOCATION: (11)..(11)
<223> OTHER INFORMATION: X = any positively charged amino acid
<220> FEATURE:
<221> NAME/KEY: MOD_RES
<222> LOCATION: (12)..(12)
<223> OTHER INFORMATION: X = L, V, I, F or W
<220> FEATURE:
<221> NAME/KEY: MOD_RES
<222> LOCATION: (13)..(13)
<223> OTHER INFORMATION: X = any positively charged amino acid

<400> SEQUENCE: 27

Xaa Xaa Xaa Xaa Xaa Xaa Xaa Xaa Xaa Xaa Xaa Xaa Xaa
1               5                   10

<210> SEQ ID NO 28
<211> LENGTH: 5
<212> TYPE: PRT
<213> ORGANISM: Artificial
<220> FEATURE:
<223> OTHER INFORMATION: Synthetic Peptide

<400> SEQUENCE: 28

Leu Leu Leu Leu Leu
1               5

<210> SEQ ID NO 29
<211> LENGTH: 11
<212> TYPE: PRT
<213> ORGANISM: Artificial
<220> FEATURE:
<223> OTHER INFORMATION: Synthetic Peptide

<400> SEQUENCE: 29

Lys Ile Lys Leu Leu Leu Leu Leu Lys Ile Lys
1               5                   10

<210> SEQ ID NO 30
<211> LENGTH: 11
<212> TYPE: PRT
<213> ORGANISM: Artificial
<220> FEATURE:
```

<223> OTHER INFORMATION: Synthetic Peptide

<400> SEQUENCE: 30

Lys Val Lys Leu Leu Leu Leu Lys Val Lys
1               5                   10

<210> SEQ ID NO 31
<211> LENGTH: 11
<212> TYPE: PRT
<213> ORGANISM: Artificial
<220> FEATURE:
<223> OTHER INFORMATION: Synthetic Peptide

<400> SEQUENCE: 31

Lys Phe Lys Leu Leu Leu Leu Lys Val Lys
1               5                   10

<210> SEQ ID NO 32
<211> LENGTH: 12
<212> TYPE: PRT
<213> ORGANISM: Artificial
<220> FEATURE:
<223> OTHER INFORMATION: Synthetic Peptide

<400> SEQUENCE: 32

Lys Leu Lys Leu Leu Leu Leu Leu Lys Leu Lys
1               5                   10

<210> SEQ ID NO 33
<211> LENGTH: 11
<212> TYPE: PRT
<213> ORGANISM: Artificial
<220> FEATURE:
<223> OTHER INFORMATION: Synthetic Peptide

<400> SEQUENCE: 33

Lys Trp Lys Trp Trp Trp Trp Trp Lys Leu Lys
1               5                   10

<210> SEQ ID NO 34
<211> LENGTH: 11
<212> TYPE: PRT
<213> ORGANISM: Artificial
<220> FEATURE:
<223> OTHER INFORMATION: Synthetic Peptide

<400> SEQUENCE: 34

Lys Trp Lys Trp Leu Leu Leu Trp Lys Trp Lys
1               5                   10

<210> SEQ ID NO 35
<211> LENGTH: 10
<212> TYPE: PRT
<213> ORGANISM: Artificial
<220> FEATURE:
<223> OTHER INFORMATION: Synthetic Peptide

<400> SEQUENCE: 35

Lys Leu Lys Leu Leu Leu Leu Lys Leu Lys
1               5                   10

<210> SEQ ID NO 36
<211> LENGTH: 5
<212> TYPE: PRT
<213> ORGANISM: Artificial
<220> FEATURE:
<223> OTHER INFORMATION: Synthetic peptide

```
<400> SEQUENCE: 36

Leu Leu Leu Leu Leu
1               5
```